United States Patent [19]

Buyniski et al.

[11] 4,018,767

[45] Apr. 19, 1977

[54] ANTI-ARRHYTHMIC AGENTS

[75] Inventors: Joseph Paul Buyniski, Syracuse, N.Y.; Alex Michael Jelenevsky, Greensboro, N.C.; Ronald Leslie Buchanan, Fayetteville, N.Y.

[73] Assignee: Bristol-Myers Company, New York, N.Y.

[22] Filed: May 22, 1975

[21] Appl. No.: 579,763

[52] U.S. Cl. .................. 260/247.2 A; 260/268 TR; 260/293.61; 260/326 C; 260/326 R; 260/343.3 R; 424/248.54; 424/250; 424/267; 424/274

[51] Int. Cl.² ............. C07D 413/06; C07D 209/94; C07D 401/06; C07D 403/06

[58] Field of Search ................ 260/326 C, 247.2 A, 260/268 TR, 293.61

[56] References Cited

UNITED STATES PATENTS 3,850,921  11/1974  Matuo et al. ................ 260/247.2 A
3,850,922  11/1974  Matuo et al. ................ 260/247.2 A
3,936,449  2/1976   Matuo et al. ................ 260/247.2 A

OTHER PUBLICATIONS

Morrison et al., Organic Chemistry, pp. 1040–1043, (1969).

*Primary Examiner*—Donald G. Daus
*Assistant Examiner*—Mary C. Vaughn
*Attorney, Agent, or Firm*—Richard R. Lloyd

[57] ABSTRACT

A series of 5-endo-(1-naphthoyloxy)-N-[amino-(lower)alkyl]bicyclo[2.2.1]heptane-2,3-di-endo-carboxylic acid imides have been found to possess unique prophylactic and therapeutic activity as anti-arrhythmia agents. An example of such a compound possessing excellent activity is 5-endo-(1-naphthoyloxy)-N-(3-dimethylaminopropyl)bicyclo[2.2.1]heptane-2,3-di-endo-carboxylic acid imide hydrochloride.

15 Claims, No Drawings

ANTI-ARRHYTHMIC AGENTS

BACKGROUND OF THE INVENTION

1. Field of the Invention

This invention relates to a novel series of 5-endo-(1-naphthoyloxy)-[amino(lower)alkyl]-bicyclo[2.2.1-]heptane-2,3-di-endo-carboxylic acid imides possessing antiarrhythmic and/or anti-fibrillatory activity.

2. Description of the Prior ARt

A. British Pat. No. 1,042,840 describes compounds having the formula

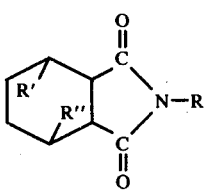

in which each of R' and R" represent hydrogen, or together an alkylene group having 1 or 2 carbon atoms, and R represents an alkyl group having 6 to 18, preferably 8 to 12 carbon atoms in a straight chain as having particularly advantageous properties as functional fluids.

B. U.S. Pat. No. 2,393,999 describes the compounds having the formula

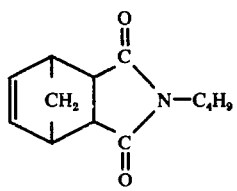

as being an effective insecticide.

C. U.S. Pat. No. 2,424,220 describes the compound having the formula

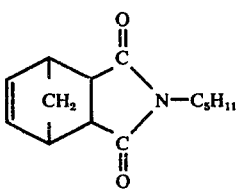

as being an effective insecticide.

D. U.S. Pat. No. 2,462,835 describes the compound having the formula

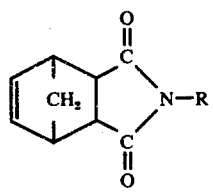

in which R is alkyl, alkene, aryl, substituted aryl, alkynyl, etc. as insecticides.

E. Culberson and Wilder, Jr., J. Org. Chem., 25, pp. 1358–62 (1960) report the preparation of compounds having the formula

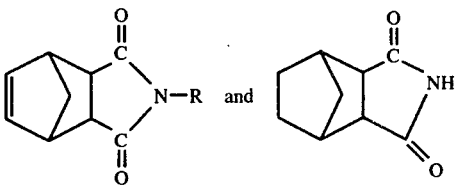

in which R is $CH_3$, $C_6H_{13}$ or hydrogen.

F. Rice, Reide and Grogan, J. Org. Chem., 19, pp. 884–893 (1954) report the preparation of compounds of the formula

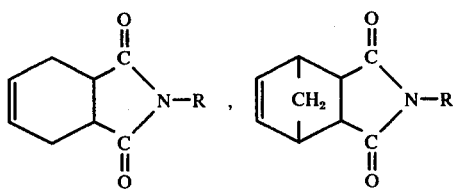

in which R is alkyl and their subsequent reduction with lithium aluminum hydride.

B. Worall, J. Am. Chem. Soc., 82, pp. 5707–5711 (1960) report the preparation of compounds having the formula

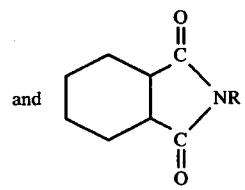

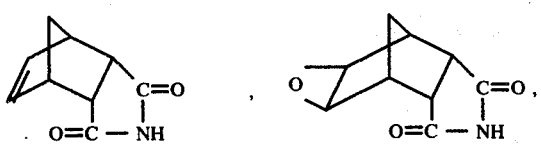

and

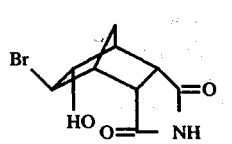

C. German Auslegeschrift No. 1,179,205 reports the preparation of compounds having the formula

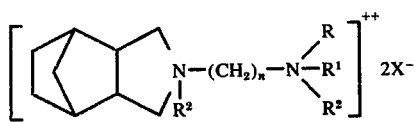

in which the bicyclo [2.2.2]octane ring system is saturated or unsaturated and/or substituted, R and $R^1$ are alkyl or alkenyl groups of 1 to 5 carbon atoms, or when combined with the nitrogen a heterocyclic ring. $R^2$ is a (lower)alkyl group, n is a number of 2 to 5 and X a halogen anion. The quaternary compounds are described as having therapeutic properties in the treatment of cardiovascular disease, specifically high blood pressure.

SUMMARY OF THE INVENTION

Compound having the formula

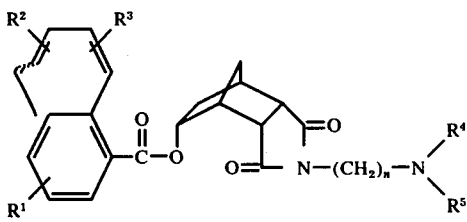

wherein $R^1$, $R^2$ and $R^3$ are alike or different and each is H, Cl, Br, F, (lower)alkyl, nitro, OH or (lower)alkoxy, $n$ is an integer of 2 to 4 inclusive and $R^4$ and $R^5$ are alike or different and each is H, (lower)alkyl or when taken together with the nitrogen a radical of the formula

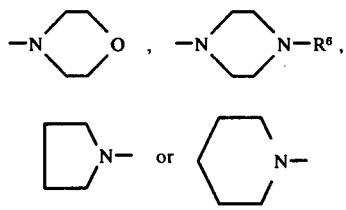

in which $R^6$ is (lower)alkyl; or a pharmaceutically acceptable acid addition salt thereof are antiarrhythmic agents.

Cardiac arrhythmia, a phenomenon commonly associated with coronary heart disease or myocardial infraction, is an affliction not uncommon in humans, especially the elderly. The mechanism of cardiac arrhythmia is suspected to be caused by an abnormal "focus" in the ventricle of the heart which sends out (fires) nerve signals more rapidly than required for the normal beating of the heart. Uncontrolled arrhythmia can lead to fibrillation which results in death.

It has been discovered that the series of compounds herein designated 5-endo-(1-naphthoyloxy)-N-[amino-(lower)alkyl]-bicyclo[2.2.1]heptane-2,3-di-endo-carboxylic acid imides having the formula

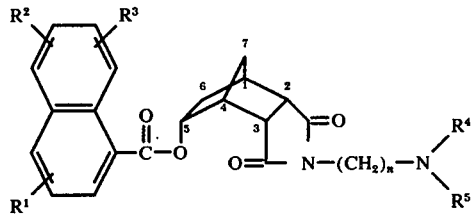

wherein $R^1$, $R^2$ or $R^3$ or H, Cl, Br, F, (lower)alkyl, nitro, OH or (lower)alkoxy, $n$ is an integer of 2 to 4 inclusive and $R^4$ or $R^5$ is H, (lower)alkyl or when taken together with the nitrogen a radical of the formula

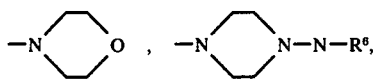

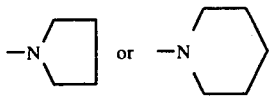

in which $R^6$ is (lower)alkyl; or a pharmaceutically acceptable acid addition salt thereof are useful therapeutic or prophylactic agents in the suppression of the abnormal ectopic beat.

Compound I can theoretically exist in several isomeric forms, namely:

A. endo-1-naphthoyloxy:endo-substituted imide;
B. exo-1-naphthoyloxy:exo-substituted imide (X);
C. endo-1-naphthoyloxy:exo-substituted imide; and
D. exo-1-naphthoyloxy:endo-substituted imide.

Furthermore, each of these isomers has two optical isomers; levorotatory and dextrorotatory.

The distinction between the isomers is determined by the relative position of the constituent bonds at positions 2, 3 and 5 of the bicyclo ring system.

When these bonds, i.e., the constituent bonds at positions 2, 3 and 5 are on the same side as the $C_7$ bridge, we have the exo-exo isomer. When these bonds, i.e., the constituent bonds at positions 2, 3 and 5 are on the opposite side of the $C_7$ bridge or alternately within the cage formed by carbon atoms 2,3, 5 and 6, then we have the endo-endo isomer. When the constituent bond at position 5 is on the same side as the $C_7$ bridge and the constituent bonds 2 and 3 are on the opposite side of the $C_7$ bridge, we have the endo-exo isomer. Illustrative of the exo-exo isomer is the compound having the formula

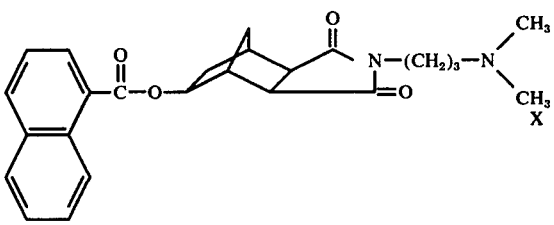

Illustrative of endo-endo is the compound of formula I.

The only isomers claimed in this invention are the endo-endo isomers as represented by compound I and the dextro- and levorotatory isomers thereof. The endo-endo isomers are inherently exclusively produced by the synthesis described herein.

The optical isomers of I can be separated and isolated by fractional crystallization of the diastereoisomeric salts formed, for instance, with (+) or (−)-tartaric acid or D-(+)camphor sulfonic acid (see experimental).

Alternatively, and probably preferably, the optical isomers of compound I can be prepared by resolving compound III by the fractional crystallization of the diastereoisomeric salts formed, for instance,, with (+) or (−) tartaric or D-(+) camphorsulfonic acid, followed by esterification to produce compound I.

For the purpose of this disclosure, the term "(lower)alkyl" is defined as an alkyl radical containing 1 to 6 carbon atoms. The term "(lower)alkoxy"is an alkoxy radical containing 1 to 6 carbon atoms. The term "pharmaceutically acceptable acid addition salt" is defined to include all those inorganic and organic acid salts of the compounds of the instant invention, which salts are commonly used to produce nontoxic salts of medicinal agents containing amine functions. Illustrative examples would be those salts formed by mixing the compounds of formula I with hydrochloric, sulfuric, nitric, phosphoric, phosphorous, hydrobromic, maleic, malic, ascorbic, citric or tartaric, pamoic, lauric, stearic, palmitic, oleic, myristic, laurylsulfonic, naphthlenesulfonic, linoleic or linolenic acid, and the like.

The compounds of the instant invention are closely related to those disclosed and claimed in the co-pending U.S. Pat. Nos. 3,850,922 and 3,850,921, in the names of our associates, Sadao Ohki and Ichiro Matuo.

The compounds of those applications are characterized by the following generic formula:

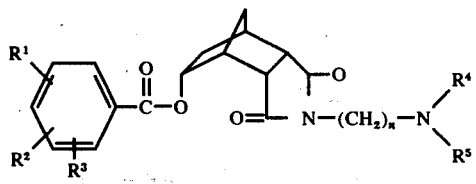

wherein $R^1$, $R^2$ or $R^3$ is H, Cl, Br, F, (lower)alkyl, nitro, OH or (lower)alkoxy, $n$ is an integer of 2 to 4 inclusive and $R^4$ or $R^5$ is H, (lower)alkyl or when taken together with the nitrogen a radical of the formula

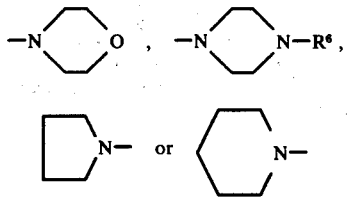

in which $R^6$ is (lower)alkyl.

As should be apparent, all the compounds of this and the other applications are esters of 5-endo-hydroxy-N-[amino(lower)alkyl]bicyclo[2.2.1]-heptane-2,3-diendo-carboxylic acid imide (III).

Subsequent to the filing of the aboveidentified applications, it was found that while those compounds of the previous applications exhibited excellent antiarrhythmia properties of moderate to long duration in rats and mice, in particular the compound (+)-5-endo-benzyloxy-(3-dimethylaminopropyl)-bicyclo[2.2.2-]heptane-2,3-endo-dicarboxylic acid imide hydrochloride, the compound only possessed activity of short duration in humans due to a particular susceptibility to an esterase found in human serum. Apparently, the compound is rapidly hydrolyzed to an inert species, identified as compound IIIa.

On receipt of this knowledge, extensive effort was expended to discover compounds that would be resistent to this enzymatic hydrolysis. It was found that 1-naphthoyloxy esters were particularly resistant to the in vivo hydrolysis. Surprisingly, however, the 2-naphthoyloxy esters were not nearly as active and exhibited signs of toxicity at low doses.

A preferred embodiment of the present invention is the compound having the formula

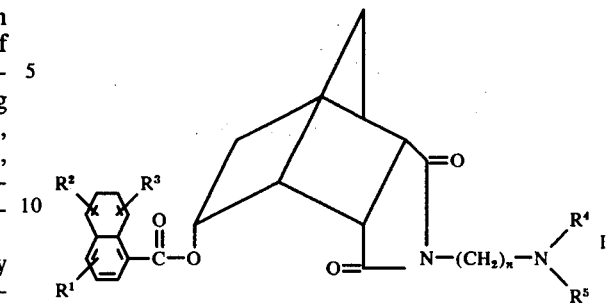

wherein $R^1$, $R^2$ and $R^3$ are alike or different and each is H, Cl, Br, F, (lower)alkyl, nitro, OH or (lower)alkoxy, $n$ is an integer of 2 to 4 inclusive and $R^4$ and $R^5$ are alike or different and each is H, (lower)alkyl or when taken together with the nitrogen a radical of the formula

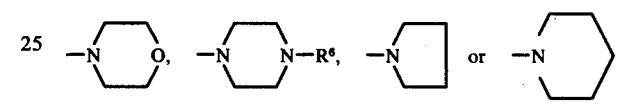

in which $R^6$ is (lower)alkyl; or a pharmaceutically acceptable acid addition salt thereof.

Another preferred embodiment of the present invention is the compound having the formula

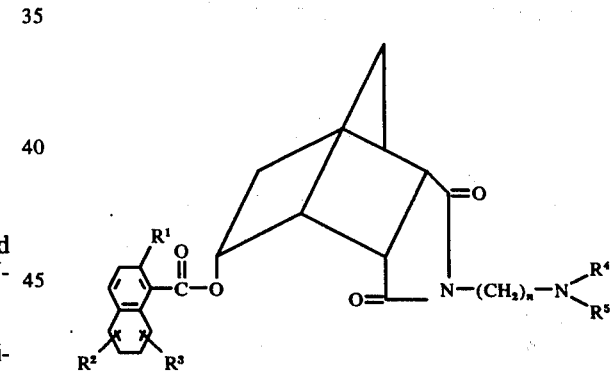

wherein $R^1$, $R^2$ and $R^3$ are alike or different and each is H, Cl, Br, F, (lower)alkyl, nitro, OH or (lower)alkoxy, $n$ is an integer of 2 to 4 inclusive and $R^4$ and $R^5$ are alike or different and each is H, (lower)alkyl or when taken together with the nitrogen a radical of the formula

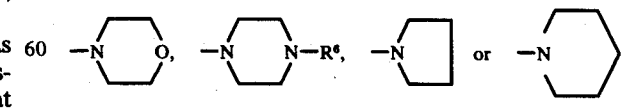

in which $R^6$ is (lower)alkyl; or a pharmaceutically acceptable acid addition salt thereof.

Another preferred embodiment is the compound having the formula

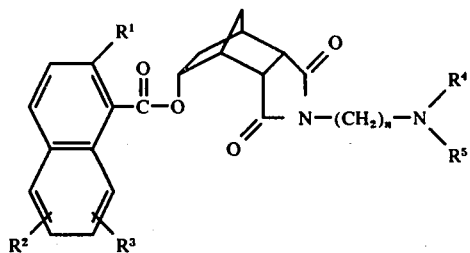

wherein $R^1$ is H or (lower)alkoxy, and $R^2$ and $R^3$ are alike or different and each is H, Cl, Br, F, (lower)alkyl, nitro, OH or (lower)alkoxy, $n$ is an integer of 2 to 4 inclusive and $R^4$ and $R^5$ are alike or different and each is H, (lower)alkyl or when taken together with the nitrogen a radical of the formula

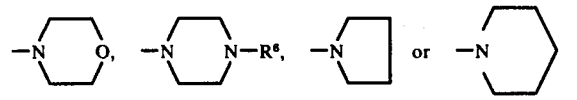

in which $R^6$ is (lower)alkyl; or a pharmaceutically acceptable acid addition salt thereof.

Another preferred embodiment of the present invention is the compound having the formula

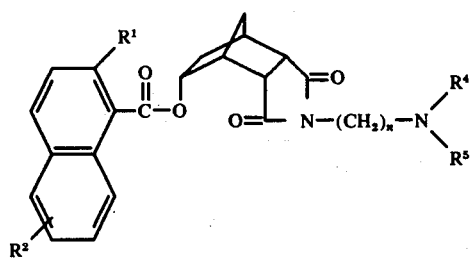

wherein $R^1$ and $R^2$ are alike or different and each is H, Cl, Br, F, (lower)alkyl, nitro, OH or (lower)alkoxy, $n$ is an integer of 2 to 4 inclusive and $R^4$ and $R^5$ are H, (lower)alkyl or when taken together with the nitrogen a radical of the formula

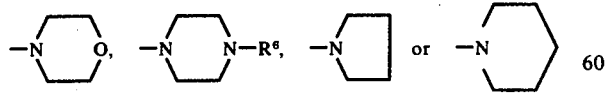

in which $R^6$ is (lower)alkyl; or a pharmaceutically acceptable acid addition salt thereof.

Another preferred embodiment of the present invention is the compound having the formula

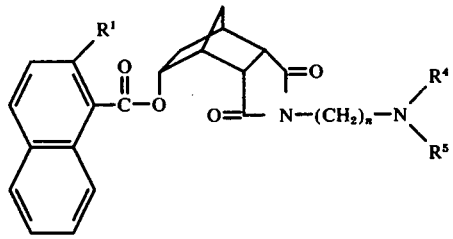

wherein $R^1$ is H, F, Cl, methoxy, ethoxy or n-propoxy, $n$ is an integer of 2 to 4 inclusive and $R^4$ and $R^5$ are alike or different and each is H, (lower)alkyl or when taken together with the nitrogen a radical of the formula

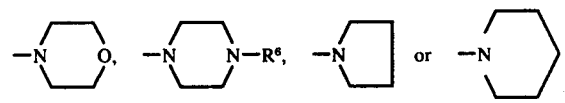

in which $R^6$ is (lower)alkyl; or a pharmaceutically acceptable acid addition salt thereof.

Another preferred embodiment of the present invention is the compound having the formula

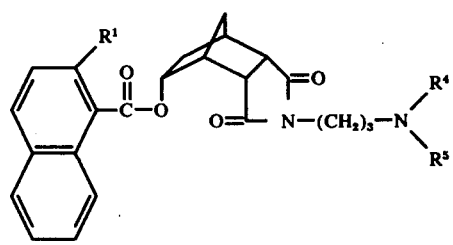

wherein $R^1$ is H, F, Cl, methoxy, ethoxy or n-propoxy, $n$ is an integer of 2 to 4 inclusive and $R^4$ and $R^5$ are alike or different and each is H or (lower)alkyl; or a pharmaceutically acceptable acid addition salt thereof.

Another preferred embodiment of the present invention is the compound having the formula in which $R^1$ is H, methoxy, or ethoxy, and $R^4$ and $R^5$ are alike or different and are H or (lower)alkyl; or a pharmaceutically acceptable acid addition salt thereof.

A most preferred embodiment of the present invention is the compound having the formula

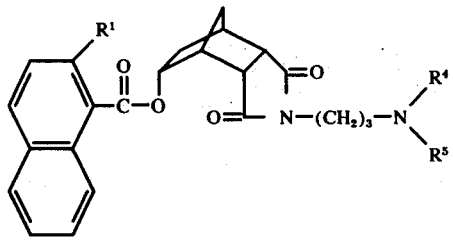

in which $R^1$ is methoxy or ethoxy, and $R^4$ and $R^5$ are alike or different and each is H, methyl or ethyl; or a pharmaceutically acceptable acid addition salt thereof.

The most preferred embodiment of the present invention is the compound having the formula

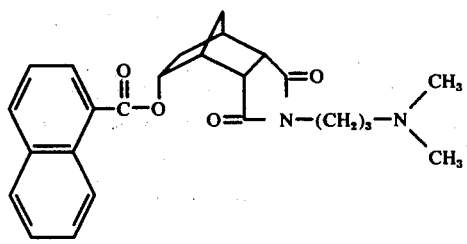

or the hydrochloride salt thereof.

Another preferred embodiment is the essentially pure dextrorotatory isomers of the compound I.

Still another preferred embodiment is the essentially pure levorotatory isomers of the compound I.

The objectives of the present invention have been achieved by the process of preparing the compounds having the formula

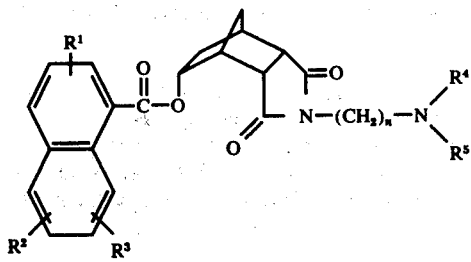

I wherein $R^1$, $R^2$ and $R^3$ are alike or different and each is H, Cl, Br, F, (lower)alkyl, nitro, OH or (lower)alkoxy, $n$ is an integer of 2 to 4 inclusive and $R^4$ and $R^5$ are alike or different and each is H, (lower)alkyl or when taken together with the nitrogen a radical of the formula

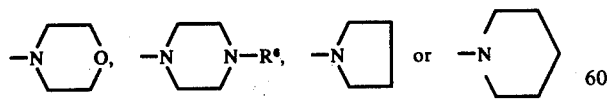

in which $R^6$ is (lwer)alkyl; which process comprises the consecutive steps of

A. treating a suspension of endo-cis-bicyclo[2.2.1-]hept-5-ene-2,3-dicarboxylic anhydride or exo-cis-bicyclo[2.2.1]hept-5-ene-2,3-dicarboxylic anhydride in water, but preferably the endo-cis isomer, with excess concentrated sulfuric acid at a temperature in the range of 70°–95° C. to produce the endo-endo compound having the formula

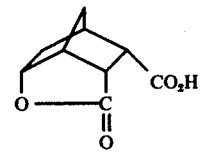

II;

B. Treating 1 mole of compound II with at least one mole of thionyl chloride or phosphorous trichloride at reflux temperature for at least 15 minutes and removing the excess thionyl chloride or phosphorous trichloride in vacuo to produce an oily residue IIa;

C. treating residue IIa with at least one mole of an amine having the formula

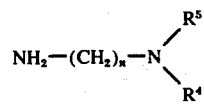

in which $n$ is an integer of 2 to 4 inclusive, $R^4$ or $R^5$ are H, (lower)alkyl or when both are taken with the nitrogen a radical of the formula

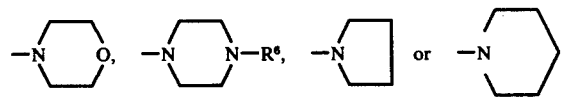

in which $R^6$ is (lower)alkyl; in an organic solvent, preferably selected from the group comprising benzene, toluene, xylene, and the like at about reflux temperatures for at least 30 minutes and removing the solvent in vacuo to produce an oily residue IIb;

D. treating residue IIb with at least one mole of potassium hydroxide in a mixture of a (lower)alkanol and water with the aid of heat, but preferably at reflux temperature for at last one hour to produce the compound having the formula

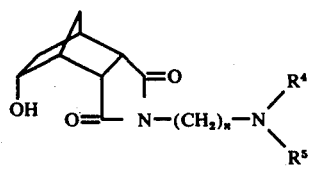

III in which $n$, $R^4$ and $R^5$ are as above, which may be resolved into its optical isomers if desired; and E. treating one mole of compound III with at least one mole of a 1-naphthoic acid halide, or its chemical equivalent, having the formula

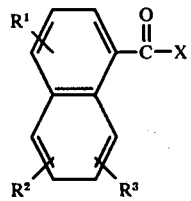

in which $R^1$, $R^2$ and $R^3$ are as defined above and X is chloro, bromo or iodo, but preferably chloro, in an organic solvent, preferably selected from the group comprising benzene, toluene, xylene, pyridine, but preferably pyridine, in a temperature range of 0° C. to 60° C., but preferably at about room temperature to yield compound I.

The compounds were tested in dogs for their reversion activity in ouabain-induced arrhythmia.

Anesthetized dogs were used for the production of ouabain-induced ventricular arrhythmias. The arrhythmia consisted of a nodal or ventricular tachycardia. The procedure used to establish the arrhythmia as well as the criteria employed to determine anti-arrhythmic activity generally was that employed by Lucchesi et al. Intravenous infusion of (±)-Ib was done at a rate of 0.2 mg./kg./min. and compared to lidocaine and quinidine. The average prolonged reverting doses are shown below.

| Compound | I. V. Reverting Dose, mg./kg.* |
|---|---|
| (±)-Ib | 2.3 ± 0.73 (N=5) |
| Quinidine | 4.9 |
| Lidocaine | 6.6 |

*Values are mean ± Standard Error; N=No. of animals.

Additionally, anti-arrhythmic activity of (±)-Ib was determined by rapid intravenous injection and compared to lidocaine, disopyramide and oprindine. The average prolonged reverting doses by rapid intravenous injection are shown below:

| Compound | I. V. Reverting Dose, mg/kg* |
|---|---|
| (±)-Ib | 0.60 ± 0.37 (N=11) |
| Lidocaine | 6.4 ± 1.4 (N=8) |
| Disopyramide | 4.5 ± 1.3 (N=6) |
| Aprindine | 2.46 ± 0.83 (N=5) |

*Values are mean ± standard error; N = No. of animals.

The compounds were also tested for their reversion of ventricular arrhythmia due to coronary artery ligation in conscious dogs:

Multifocal ventricular ectopic rhythms were produced in dogs according to the coronary artery ligation method of Harris[2]. Approximately 24 hours after induction of the ventricular arrhythmia the test drugs were infused at a rate of 0.2 mg./kg./min. The approximate average doses necessary to produce a 50% decrease in the number of ventricular ectopic beats, and to produce reversion of the ventricular arrhythmia are shown below. In contrast to 1 and 2, no reversion was observed with an intravenous infusion of lidocaine or quinidine in doses of up to 20 mg./kg.

| Compound | I.V. Dose Producing 50% Reduction in Ectopic Beats (mg./kg.) | I.V. Reverting Dose (mg./kg.) |
|---|---|---|
| (±)-Ib | 2.3 (N=7) | 10–15 (N=7) |
| Aprindine | 3.5 (N=3) | 10 (N=3) |
| Lidocaine | >20 (N=5) | >20 (N=5) |
| Quinidine | 10 (N=5) | >20 (N=5) |

*Values are means, N = No. of experiments.

Local anesthetic activity was determined by using the general method of Bulbring et al[3], in conscious guinea pigs. Intradermal injections of lidocaine and (±)-Ib were made on the back, and 30 minutes later, the animals were tested for their reaction to pain from stimuli applied with a hypodermic needle. The doses necessary to produce a 50% decrease in reaction to pain are shown below along with the confidence limits.

| Local Anesthetic Activity in Guinea Pigs | |
|---|---|
| Compound | $ED^{50}$ in mmoles of drug |
| (±)-Ib | 23 (17–32) |
| lidocaine | 23 (16–32) |

References

1. Lucchesi, B. L. and H. F. Hardman: The influence of dichloroisoproterenol (DCI) and related compounds upon ouabain and acetylstrophanthidin induced cardiac arrhythmias. J. Pharmacol. Exp. Therap., 132:372, 1961.
2. Harris, A. S.: Delayed development of ventricular ectopic rhythms following experimental coronary occlusion. Circulation 1:1318, 1950.
3. Bulbring, E. and I. Wajda: Biological comparison of local anesthetics, J. Pharmacol Exp. Therap., 85:78, 1941.

All the compounds within the scope of the present invention possess anti-arrhythmic activity.

The compounds of the present invention are useful in the treatment of cardiac arrhythmia in mammals, including man, as prophylactic or therapeutic agents in doses in the range of 0.25 mg. to 3.0 mg./kg. up to 3 or 4 times a day.

EXPERIMENTAL

EXAMPLE 1

Preparation of Bicyclo[2.2.1]heptane-endo-2,3-dicarboxylic acid-5-endo-hydroxy-γ-lactone (II)

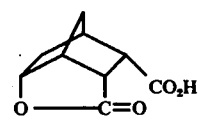

Five hundred grams (500 g.) of concentrated sulfuric acid was slowly added with vigorous stirring to a suspension of 164 g. of endo-cis-bicyclo[2.2.1]hept-5-ene-2,3-dicarboxylic anhydride in 500–600 ml. of water. The reaction was exothermic and the temperature rose to about 80°–90° C. during the addition of the sulfuric acid. Two liters of boiling water was added to the reaction solution and it was immediately filtered. As the filtrate was cooled, colorless platlets of the title product (II) crystallized. On completion of the crystallization, the crystals were collected by filtration and washed with cold water to produce 138 grams of air-dried crystals, m.p. 200° C.

EXAMPLE 2

General Method of Preparation of 5-endo-Hydroxy-N-[amino(lower)alkyl]bicyclo[2.2.1-]heptane-2,3-di-endo-carboxylic Acid Imides (III)

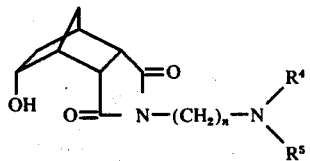

III

A mixture of 0.1 mole of lactone (II) from example 1 and 50 ml. of thionyl chloride was refluxed on a water bath for two hours. The excess thionyl chloride was removed in vacuo and an oily residue (IIa) remained that was washed with n-hexane (or petroleum ether). The oily residue was dissolved in 50 ml. of anhydrous benzene. To this solution was added a solution of 0.12 moles of the appropriate amine, e.g., N,N-dimethylaminopropylamine, and 100 ml. of anhydrous benzene with stirring. The mixture was then refluxed for about five hours and concentrated in vacuo. The resultant brown syrupy substance (IIb) was refluxed for five hours in 300 ml of of 50% water-ethanol containing 0.12 mole of potassium hydroxide ethanol. The solvents were removed in vacuo, saturated potassium carbonate solution added and the resultant solution extracted repeatedly using chloroform or 1:1 ethyl acetate-benzene. The collective organic extracts were washed with saturated sodium chloride solution and dried over anhydrous sodium sulfate. After filtration, the solution was concentrated in vacuo and the product was recovered by crystallization, chromatography and-/or vacuum distillation wherein in formula III, $n$ is an integer of 2 to 4 inclusive, $R^4$ or $R^5$ is H, (lower)alkyl or when taken together with the nitrogen a radical of the formula

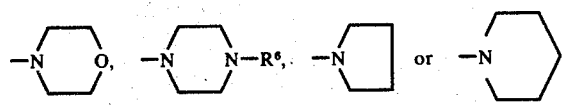

in which $R^6$ is (lower)alkyl.

EXAMPLE 3

General Method of Preparation of 5-endo-(1-naphthoyloxy)-N-[amino(lower)alkyl]bicyclo[2.2.1]heptane-2,3-di-endo-carboxylic Acid Imides (I)

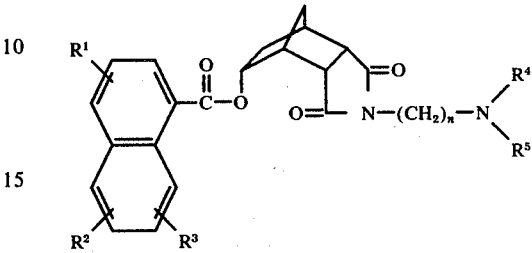

I

The 5-endo-Hydroxy-N[amino(lower)alkyl]bicyclo[2.2.1]heptane-2,3-di-endo-carboxylic acid imide (III) (0.01 mole) obtained in example 2 was added to 50 ml. of a 100:1 pyridine-piperidine solution of 0.012 mole of an appropriate α-naphthoyl halide, e.g., 1-naphthoic acid chloride, with stirring. The resultant mixture was allowed to stand overnight in a refrigerator or warmed in a water or oil bath. The mixture was poured into ice-water and saturated with sodium carbonate and then extracted with chloroform or 1:1 benzene-ethyl acetate. The combined organic extracts were washed with saturated sodium chloride solution and dried over anhydrous sodium sulfate. The solution was collected by filtration and concentrated in vacuo to yield the desired title product (I).

EXAMPLE 4

Alternate Method of Preparation of 5-endo-Hydroxy-N-[amino(lower)alkyl]bicyclo[2.2.1-]heptane-2,3-di-endo-carboxylic Acid Imides (III)

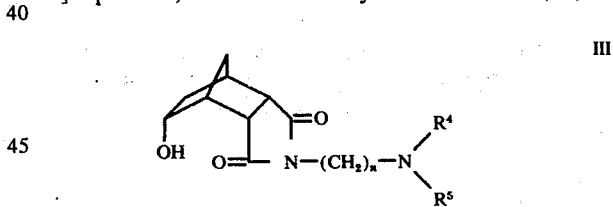

III

A mixture of 0.1 mole of lactone (II) from example 1 above and 30 ml. of PCl₃ was refluxed in a water bath for 2 hours. The excess PCl₃ was removed in vacuo and washed with n-hexane. The oily residue was dissolved in 50 ml. of chloroform or methylene chloride and a solution of 0.12 mole of an appropriate amine, e.g., N,N-dimethylaminopropylamine, dissolved in 100 ml. of anhydrous chloroform or methylene chloride was added with stirring and cooling. Stirring was continued for two hours, following which the mixture was warmed to room temperature following which the mixture was refluxed for about 15 minutes. The solution was washed with saturated potassium carbonate solution after cooling, separated, and the organic phase washed with saturated sodium chloride solution. The organic solution was dried over anhydrous sodium sulfate, filtered, and concentrated in vacuo. The material subsequently collected was the title product of formula III wherein $n$ is an integer of 2 to 4 inclusive, $R^4$ or $R^5$ is H, (lower)alkyl or when taken together with the nitrogen a radical of the formula

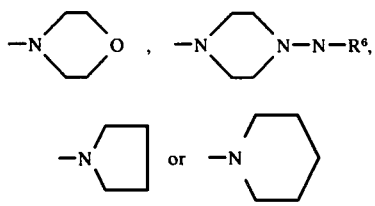

in which R⁶ is (lower)alkyl.

EXAMPLE 5

Preparation of 5-endo-Hydroxy-N-(3-dimethylaminopropyl)-bicyclo[2.2.1]-heptane-2,3-di-endo-carboxylic Acid Imide (IIIa)

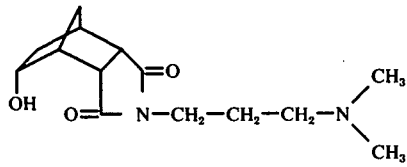

IIIa

Substitution in the procedure of example 2 or 4 of an equimolar quantity of N,N-dimethylaminopropylamine for the "appropriate" amine used therein produced the title product as colorless plates when crystallized from ethanol-n-hexane; m.p. 148° C. (1¾ $H_2O$) or 154° C. (⅛ $H_2O$). Yield: 26–37%.

Anal. calc'd. for $C_{14}H_{22}O_3N_2$ 1.3/4$H_2O$: C, 56.42; H, 8.79; N, 9.40. Found: C, 56.70; H, 8.76; N, 9.11.

Anal. calc'd. for $C_{14}H_{22}O_3N_2$.⅛ $H_2O$: C, 61.76; H, 8.45; N, 10.29. Found: C, 61.93; H, 8.76; N, 10.40.

EXAMPLE 6

(±)-5-Endo-(1-naphthoyloxy)-N-(3-dimethylaminopropyl)-bicyclo[2.2.1]heptane-2,3-di-endo carboxylic acid imide hydrochloride (Ib)

To a solution of the (±)-IIIa (5.32 g, 0.02 mole) in dry pyridine (35 ml) was added a solution of 1-naphthoic acid chloride (7.60 g, 0.04 mole; prepared in the standard manner from 1-naphthoic acid and thionyl chloride) in dry pyridine (20 ml). The mixture was stirred under anhydrous conditions at 25° for 19 hours, whereupon the pyridine was removed under reduced pressure. The residue was then dissolved in 100% ethanol (200 ml), HCl gas was bubbled in and the solvent was stripped off under reduced pressure. The resultant crude solid was recrystallized from 100% ethanol, affording 4.4 g (53%) of the desired product Ib after drying under vacuum over $P_2O_5$; mp 218°–219°.

Anal. Calc'd. for $C_{25}H_{28}N_2O_4$ HCl: C, 65.71; H, 6.40; N, 6.13; Cl, 7.76. Found: C, 65.72; H, 6.30; N, 6.35; Cl, 7.98.

EXAMPLE 7

General Method of Preparation of 5-endo-benzoyloxy-N-[amino(lower)alkyl]bicyclo[2.2.1]heptane-2,3-di-endo-carboxylic Acid Imides (L) (Starting Materials)

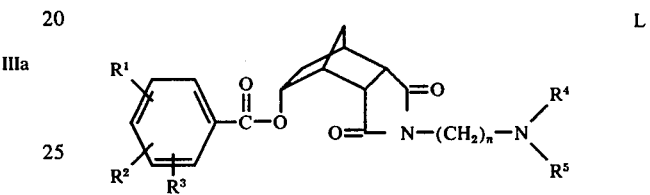

L

The 5-endo-Hydroxy-N-[amino(lower)alkyl]-bicyclo[2.2.1]heptane-2,3-di-endo-carboxylic acid imide (III) (0.01 mole) obtained in example 2 was added to 50 ml. of a 100:1 pyridine-piperidine solution of 0.012 mole of an appropriate benzoyl halide, e.g., benzoyl chloride, with stirring. The resultant mixture was allowed to stand overnight in a refrigerator or warmed in a water or oil bath. The mixture was poured into ice-water and saturated with sodium carbonate and then extracted with chloroform or 1:1 benzene-ethyl acetate. The combined organic extracts were washed with saturated sodium chloride solution and dried over anhydrous sodium sulfate. The solution was collected by filtration and concentrated in vacuo to yield the desired title product (L).

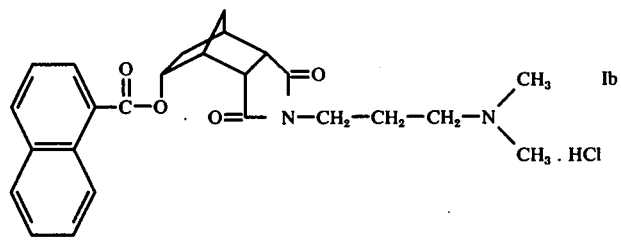

Ib

EXAMPLE 8

Preparation of
5-endo-Benzoyloxy-N-(3-dimethylaminopropyl)bicyclo[2.2.1]heptane-2,3-di-endo-carboxylic Acid Imide (Lb)

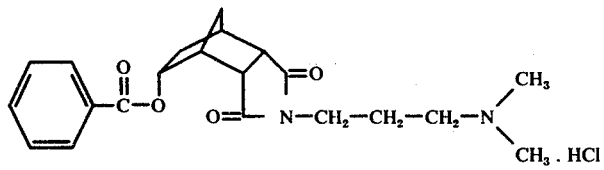

A. Substitution in the procedure of example 8 of an equimolar quantity of benzoyl chloride for the "appropriate" benzoyl halide used therein and for the dicarboxylic acid imide III an equimolar quantity of IIIa obtained in example 5 produced the title product which was collected as the hydrochloride salt.

B. The free base was dissolved in near boiling ethanol (700 ml.) and 90 ml. of ethanol saturated with hydrogen chloride gas was added. The solution was cooled with ice to produce colorless plates of the hydrochloride salt of formula Lb; m.p. 239° C. with decomposition upon recrystallization from methanol-acetone. Yield-90%.

Anal. calc'd. for $C_{21}H_{27}O_4N_2Cl \cdot \frac{1}{3} H_2O$: C, 61.07; H, 6.83; N, 6.95. Found: C, 60.63; H, 6.88; N, 7.33.

EXAMPLE 9

Resolution of
(±)-5-endo-Benzoyloxy-N-(3-dimethylaminopropyl)-bicyclo[2.2.1]heptane-2,3-di-endo-carboxylic Acid Imide Hydrochloride (Lb)

I. Preparation of the (−)-enantiomer

A.
(±)-5-endo-Benzoyloxy-N-(3-dimethylaminopropyl)-bicyclo[2.2.1]heptane-2,3-di-endo-carboxylic Acid Imide (Lb)

A stirred mixture of the hydrochloride salt of Lb (10 g.) in water (150 ml.) and ether (200 ml.) was neutralized by the addition of sodium carbonate. The aqueous layer was re-extracted with ether (2 × 200 ml.). The combined ethereal extracts were washed with water, followed by water saturated with sodium chloride (3×) and dried (sodium sulfate). Removal of the ether left colorless crystals of the racemic base Lb (9.3 g.), m.p. 106°–107.5°.

B.(±)-10-Camphorsulfonic acid salt of
(−)-5-endo-benzoyloxy-N-(3-dimethylaminopropyl)-bicyclo[2.2.1]heptane-2,3-di-endo-carboxylic Acid Imide A hot solution of (+)-10-camphorsulfonic acid (276.5 g., 1.19 mole) in ethanol (1.1.1) was added to a hot solution of the racemic base Lb (441.1 g., 1.19 mole) in ethanol (3.5.1) containing water (175 ml.). The solution was heated to near boiling and then rapidly cooled to 20°. The colorless crystalline material which formed during 3 hours standing at 20° was collected and washed with cold ethanol (600 ml.) to give 325.3 g. of the title product, m.p. 221°–226°. The salt was recrystallized from acetonitrile to give colorless needles (282.6 g.), m.p. 230°–233°. The ethanolic mother liquor was retained for isolation of the (+)-isomer.

C.
(−)-5-endo-Benzoyloxy-N-(3-dimethylaminopropyl)-bicyclo[2.2.1]heptane-2,3-di-endo-carboxylic Acid Imide [(−)-Lb].

The camphorsulfonic acid salt from step B (282.6 g.) was partitioned between a stirred mixture of ethyl acetate (3.5.1) and water (3.1) containing sodium carbonate (150 g.). The aqueous layer was reextracted with ethyl acetate (600 ml.). The combined ethyl acetate extracts were washed with water saturated with sodium chloride (3×), and dried (sodium sulfate). Removal of the ethyl acetate left the title product as colorless crystals (173.3 g.): m.p. 131.5°–132.5°; $[\alpha]_D^{25} -78.53°$ (c. 4.26, ethanol).

D.
(−)-5-endo-Benzoyloxy-N-(3-dimethylaminopropyl)-bicyclo[2.2.1]heptane-2,3-di-endo-carboxylic Acid Imide Hydrochloride (V)

To a near boiling solution of the (−)-isomer (173.3 g., 0.468 mole) from step C in 95% ethanol (3.5.1) was added 475 ml. of 95% ethanol, 0.988 molar in hydrogen chloride (0.468 mole of HCl). The solution was cooled in ice. The colorless crystals were collected, washed with cold 95% ethanol (600 ml.) and dried to give the title product (182.6 g.): m.p. 207°–209°; $[\alpha]_D^{25} -85.56°$ (c. 1.5, water). The m.p. and rotation were not significantly changed upon further recrystallization from 95% ethanol.

II. Preparation of the (+)-enantiomer.

A. (−)-Tartaric Acid Salt of
(+)-5-endo-benzoyloxy-N-(3-dimethylaminopropyl)-bicyclo[2.2.1]heptane-2,3-di-endo-carboxylic Acid Imide.

The ethanolic mother liquor from step I B. above was stored at 0° for 90 hours to give additional crystalline material (237.2 g.), m.p. 183°–186°. The filtrate was concentrated to give another crop of colorless crystals (119.9 g.), m.p. 168°–177°. Both crops were combined and partitioned between ethyl acetate and aqueous sodium carbonate as described in I C. above to give a mixture of (+)- and (−)-isomers (221.4 g.), m.p. 125°–129°, greatly enriched in the (+)-enantiomer.

(−)-Tartaric acid (89.6 g., 0.596 mole) was added to a hot stirred solution of the (+)-enriched mixture (221.4 g., 0.596 mole) in ethanol (3.6.1) containing water (40 ml.). The stirred mixture was heated to near boiling and then cooled to 25° during 4 hours. The colorless crystalline material was collected, washed with cold 195% ethanol (500 ml.) and dried to give the tartrate salt of the (+)-enantiomer (291.6 g.), m.p. 157°–161° (dec.). Recrystallization from acetonitrile gave 247.2 g. of the purified tartrate salt, m.p. 162°–164° (dec.).

B.
(+)-5-endo-Benzoyloxy-N-(3-dimethylaminopropyl)-bicyclo[2.2.1]heptane-2,3-di-endo-carboxylic Acid Imide [(+)-Lb]

The tartrate salt from step A (247.2 g.) was decomposed with aqueous sodium carbonate and the liberated (+)-enantiomer extracted into ethyl acetate as described in I.C. Removal of the ethyl acetate left the (+)-isomer (171.6 g.), as colorless crystals: m.p. 131°–133.5°; $[\alpha]_D^{25}+ 77.74°$ (c. 1.89, ethanol).

C.
(+)-5-endo-Benzoyloxy-N-(3-dimethylaminopropyl)-bicyclo[2.2.1]heptane-2,3-di-endo-carboxylic Acid Imide Hydrochloride (VI)

The (+)-enantiomer (171.6 g.) from step B was treated with an equivalent of ethanolic hydrogen chloride as described for the (−)-enantiomer in I D. to give colorless crystals of the (+)-enantiomer HCl, (188.2 g.): m.p. 207°–209°; $[\alpha]_D^{25}+85.88°$ (c. 1.36, water).

EXAMPLE 10
(+)-5-Endo-(1-naphthoyloxy-N-(3-dimethylaminopropyl)-bicyclo[2.2.1]heptane-2,3-di-endo-carboxylic acid imide hydrochloride [(+)-Ib].

A.
(+)-5-Endo-Hydroxy-N-(3-dimethylaminopropyl)-bicyclo[2.2.1]heptane-2,3-di-endo-carboxylic acid imide [(+)-IIIa]

(+)-5-Endo-benzoyloxy-N-(3-dimethylaminopropyl)-bicyclo[2.2.1]heptane-2,3-di-endo-carboxylic acid imide hydrochloride (3.65 g, 0.0086 mole) [(+)-Lb] was suspended in 18.8 ml of 1.0N NaOH and heated to reflux with stirring for 45 minutes in an oil bath at 120°–125° C. The solution was then cooled, filtered and evaporated under reduced pressure to yield a white solid. The solid was then triturated with three 80 ml aliquots of hot EtOAc. The aliquot were combined and evaporated to yield an oil which solidified upon cooling. The solid was then resuspended in 100 ml cyclohexane and 15 ml EtOAc and heated to a reflux. Filtration of the hot solution and cooling to 20° C yielded a crystalline solid (1.53 g; 67% mp 121°–122° C determined to be (+)-IIIa.

B.
(+)-5-Endo-(1-Naphthoyloxy)-N-(3-dimethylaminopropyl)-bicyclo[2.2.1]heptane-2,3-endo-carboxylic acid imide hydrochloride [(+)-Ib]

Substitution in the procedure of example 6 for the (±)-IIIa used therein of an equimolar quantity of (±)-IIIa produced the title compound (+)-Ib; 53%; m.p. 178°–179° C.

Anal. Calc'd. for $C_{25}H_{28}N_2O_4 \cdot HCl$: C, 65.71; H, 6.40; N, 6.13; Cl, 7.76. Found: (Corrected for 2.18% $H_2O$) C, 65.54; H, 6.56; N, 5.96; Cl 8.02. $[\alpha]_{589}^{25°}=+69.44$ (C = 0.161 g; $H_2O$)

EXAMPLE 11
(−)-5-Endo-(1-naphthoyloxy)-N-(3-dimethylaminopropyl)-bicyclo[2.2.1]heptane-2,3-di-endo-carboxylic acid imide hydrochloride [(−)-Ib]

A.
(−)-5-Endo-Hydroxy-N-(3-dimethylaminopropyl)bicyclo[2.2.1]heptane-2,3-di-endo-carboxylic acid imide [(−)-IIIb]

Substitution in the procedure of example 10A for the compound (+)-Lb used therein of an equimolar quantity of (−)-Lb produced compound (−)-IIIb; m.p. 119°–120° C.

B. Substitution in the procedure of example 10B for the compound (+)-IIIb used therein of an equimolar quantity of compound (−)-IIIb produced the compound (−)-Ib in 42% yield; m.p. 177°–178° C.

Anal. calc'd. for $C_{25}H_{28}N_2O_4 \cdot HCl$: C, 65.71; H, 6.40; N, 6.13; Cl, 7.76. Found: (Corrected for 4.41% $H_2O$)C, 65.58; H, 6.69; N, 6.26; Cl, 8.31. $[\alpha]_{589}^{25°}=-69.68$ (C = 0.064 g; $H_2O$).

EXAMPLE 12
(±)-5-Endo-(2-naphthoyloxy)-N-(3-dimethylaminopropyl)-bicyclo[2.2.1]heptane-2,3-di-endo-carboxylic acid imide hydrochloride [(±)-Ic]

Substitution in the procedure of example 6 for the 1-naphthoic acid chloride used therein of an equimolar quantity of 2-naphthoic acid chloride produced the title compound (35)-Ic. The free base was converted to the hydrochloride salt by the addition of a solution of $CHCl_3$ saturated with dry HCl gas to $CHCl_3$ solution of (±)-Ic. The solvent was removed in vacuo and the residue was crystallized from 1:1 ethyl acetate-100% ethanol; m.p. 195°–196° C.

Anal. calc'd. for $C_{25}H_{28}N_2O_4 \cdot HCl$: C, 65.71; H, 6.40; N, 6.13; Cl, 7.76. Found: C, 66.04; H, 6.61; N, 6.30; Cl, 7.65.

EXAMPLE 13
Preparation of 5-endo-Hydroxy-N-(2-dimethylaminoethyl)bicyclo[2.2.1]heptane-2,3-di-endo-carboxylic Acid Imide (IIIb)

Substitution in the procedure of example 4 for the "appropriate" amine used therein of an equimolar quantity of N,N-dimethylethylamine produced the title product. The free base was collected as colorless plates upon recrystallization from ethanol-n-hexane; m.p. 141.5° C. Yield: 50%

Anal. calc'd. for $C_{13}H_{20}O_3N_2 \cdot 1/3H_2O$: C, 60.46; H, 8.13; N, 10.85. Found: C, 60.71; H, 8.04; N, 10.95.

EXAMPLE 14
Preparation of 5-endo-Hydroxy-N-(2-diethylaminoethyl)bicyclo[2.2.1]heptane-2,3-di-endo carboxylic Acid Imide Phenolphthalinate (IIIc)

Substitution in the procedure of example 2 for the "appropriate" amine used therein of an equivalent amount of N,N-diethylaminoethylamine produced the title product as yellow oil, b.p. 213°–220° C./5 mm. Hg. Yield: 37%. The product was further characterized as the phenolphthalinate salt, m.p. 137°–138.8° C.

Anal. calc'd. for $C_{35}H_{40}O_7N_2 \cdot 1½H_2O$: C, 67.04; H, 6.91; N, 4.48. Found: C, 67.38; H, 7.41; N, 4.23

EXAMPLE 15

Preparation of 5-endo-Hydroxy-N-(3-diethylaminopropyl)bicyclo[2.2.1]heptane-2,3-di-endo-carboxylic Acid Imide Phenolphthalinate (IIIf).

Substitution in the procedure of example 2 for the "appropriate" amine used therein of an equivalent amount of N,N-diethylaminopropylamine produced the title product as a yellow oil, b.p. 228°–230° C./6 mm. Hg. Yield: 34%. The product was further characterized as the phenolphthalinate salt, m.p. 155°–158° C.

Anal. calc'd. for $C_{36}H_{42}O_7N_2.1 \frac{1}{2} H_2O$: C, 67.39; H, 7.02; N, 4.36. Found: C, 67.77; H, 6.79; N, 4.36.

EXAMPLE 16

Preparation of 5-endo-Hydroxy-N-(3-piperidino propyl)bicyclo[2.2.1]heptane-2,3-di-endo-carboxylic Acid Imide (IIIe)

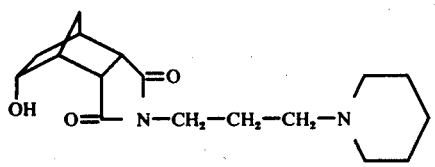

IIIe substitution in the procedure of example 4 for the "appropriate" amine used therein of an equivalent amount of 3-piperidinopropylamine produced the title product as colorless plates upon recrystallization from isopropanol-n-hexane, m.p. 121.5° C. Yield: 50%.

Anal. calc'd. for $C_{17}H_{26}O_3N_2.\frac{1}{4}H_2O$: C, 65.70; H, 8.53; N, 9.01. Found: C, 66.05; H, 9.03; N, 9.06.

EXAMPLE 17

Preparation of 5-endo-Hydroxy-N-(2-morpholinoethyl)bicyclo[2.2.1-]heptane-2,3-di-endo-carboxylic Acid Imide Hydrochloride (IIIf)

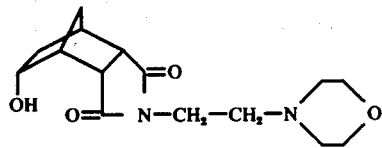

IIIf

Substitution in the procedure of example 2 or 4 for the "appropriate" amine used therein of an equivalent amount of morpholinoethylamine produced the title compound which was collected as the hydrochloride. The hydrochloride salt was prepared by dissolving IIIf in a minimal amount of diethylether solution of dry HCl gas to the solution of IIIf with stirring and scratching. The resultant precipitate was collected by filtration. The hydrochloride was collected as colorless plates upon recrystallization from water-ethanol, m.p. 280°–282° C. Yield: 30–34%.

Anal. calc'd. for $C_{15}H_{22}O_4N_2.HCl$: C, 54.43; H, 7.00; N, 8.46. Found: C, 54.26; H, 7.56; N, 8.50.

EXAMPLE 18

Preparation of 5-endo-Hydroxy-N-(3-morpholinopropyl)bicyclo[2.2.1]heptane-2,3-di-endo-carboxylic Acid Imide (IIIg)

Substitution in the procedure of example 2 for the "appropriate" amine used therein of a equivalent amount of morpholinopropylamine produced the title product as a yellow oil, b.p. 260°–270° C./4 mm. Hg.; yield 50%. The product was further characterized as the methiodide salt; m.p. 233° C.

Anal. calc'd. for $C_{16}H_{24}O_4N_2.CH_3I$: N, 6.20. Found: N, 6.28.

EXAMPLE 19

Preparation of 5-endo-(2-ethoxy-1-naphthoyloxy)-N-(3dimethylaminopropyl)-bicyclo[2.2.1]heptane-2,3-di-endo-carboxylic acid imide hydrochloride [(±)-Id]

Substitution in the procedure of example 6 for the 1-naphthoic acid chloride used therein of an equimolar quantity of 2-ethoxy-1-naphthoic acid chloride produces the title product (±)-Id.

EXAMPLE 20

Preparation of 5-endo-(2-methoxy-1-naphthoyloxy)-N-(3-dimethylaminopropyl)-bicyclo[2.2.1]heptane-2,3-di-endo-carboxylic acid imide hydrochloride [(±)-Ie]

Substitution in the procedure of example 6 for the 1-naphthoic acid chloride used therein of an equimolar quantity of 2-methoxy-1-naphthoic acid chloride produces the title product (±)-Ie.

EXAMPLE 21

Preparation of 5-endo-(1-naphthoyloxy)-N-(3-morpholinopropyl)-bicyclo[2.2.1]heptane-2,3-di-endo-carboxylic acid imide (±) (Ig).

Substitution in the procedure of example 3 for the dicarboxylic acid imide III used therein of an equimolar quantity of IIIg produces the title product (±)-Ig.

EXAMPLE 22

Preparation of 5-endo-(1-naphthoyloxy)-N-(2-dimethylaminoethyl)-bicyclo[2.2.1]heptane-2,3-di-endo-carboxylic Acid Imide (±) (Ij)

Substitution in the procedure of example 6 for the dicarboxylic acid imide used therein of an equimolar quantity of IIIb obtained in example 13, produces the title compound (±)-Ij.

EXAMPLE 23

Preparation of 5-endo-(1-naphthoyloxy)-N-(3-piperidinopropyl)bicyclo[2.2.1]heptane-2,3-di-endo-carboxylic Acid Imide (Ik)

Substitution in the procedure of example 3 for the dicarboxylic acid imide III used therein of an equimolar quantity of IIIe produced the title compound.

EXAMPLE 24

Preparation of
5-endo-(1-naphthoyloxy)-N-(3-methylaminopropyl)-bicyclo[2.2.1]heptane-2,3-di-endo-carboxylic Acid Imide Hydrochloride (Ij)

A.
5-endo-(1-naphthoyloxy)-N-[3-(2,2,2-trichloroethoxycarbonyl)-3-methylaminopropyl]bicyclo[2.2.1]heptane-2,3-di-endo-carboxylic Acid Imide Under ahydrous conditions, there is added 4.66 g. (22 mmoles) of trichloroethyl chloroformate to a mixture of 3.7 g. (10 mmoles) of compound (±)-Ib and 2.0 g. (14.5 mmoles) potassium carbonate in 50 ml. benzene. The reaction mixture is refluxed for 18 hours. After cooling, ethyl acetate is added and the solution is filtered from the insolubles. The filtrate is washed with water, 5% $K_2CO_3$, water, 5% HCl, water and brine. After drying ($Na_2SO_4$) and filtration, the solvents are evaporated. In this manner, there is obtained a crude product which is the title product.

B.
5-endo-(1-naphthoyloxy)-N-(3-methylaminopropyl)-bicyclo[2.2.1]heptane-2,3-di-endo-carboxylic Acid Imide Hydrochloride Zinc dust (11.0 grams) is added to a solution of 5.56 g (10.5 mmoles) of the compound prepared in A above in 120 ml. of 90% acetic acid. The resulting reaction mixture is stirred at room temperature for 4 hours. The mixture is filtered and the filtrate evaporated to dryness. The residue is made basic by the addition of sodium bicarbonate and again is evaporated to dryness. Benzene (500 ml.) and $Na_2SO_4$ is added to the residue. The mixture is filtered; the filtrate is evaporated and the residue is dissolved in methanol. Some ether is added, and the hydrochloride salt is prepared with anhydrous hydrogen chloride gas. The precipitated salt is collected and after several recrystallizations from methanol-ether, there is obtained the title compound (Ij).

EXAMPLE 25

Preparation of
5endo-(1naphthoyloxy)-N-(3-aminopropyl)bicyclo[2.2.1]heptane-2,3-di-endo-carboxylic acid imide (Ik)

A.
5-endo-Hydroxy-bicyclo[2.2.1]heptane-endo-2[N-(2-cyanoethyl)]carboxamide-endo-3-carboxylic acid γ-lactone (XX).

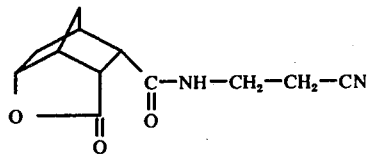

XX

A mixture of lactone-acid II (18.2 g; 0.1 mole), 150 ml. $SOCl_2$ and 250 ml $CH_2Cl_2$ containing 4 drops of DMF (dimethylformamide) was refluxed (60° C) for 3 hours. After evaporating to dryness, benzene was added and removed under reduced pressure. After dissolving the acid chloride in 350 ml $CH_2Cl_2$, there was added dropwise with vigorous stirring a solution of 3-aminopropionitrile (15.3 g; 0.21 mole) in 150 ml $CH_2Cl_2$. The resulting reaction mixture was refluxed for 2 hours. After cooling and filtering the insoluble materials, the filtrate was evaporated to dryness. The residue, so obtained, was slurried with a small amount of $CH_3CN$ to which ether was carefully added. In this way, the crystalline product was obtained in 85.5% yield with mp 129°–135° C. A sample on recrystallization from $CH_3CN$ gave analytically pure material, mp 145°–147° C.

Anal. calc'd. for $C_{12}H_{14}N_2O_3$: C, 61.52; H, 6.02; N, 11.96. Found: C, 61.54; H, 6.28; N, 11.96.

B.
5-endo-(1-naphthoyloxy)-N-(2-cyanoethyl)bicyclo[2.2.1]heptane-endo-2,3-dicarboxylic acid imide (XI)

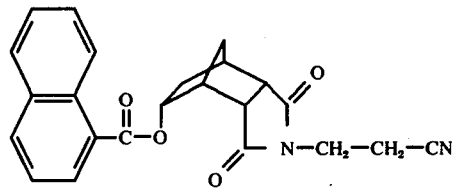

XI

To a solution of lactone-amide XX (16 g; 0.068 mole) in 200 ml pyridine is added slowly the 1-naphthoic acid chloride (14.4 g; 0.102 mole). The resulting reaction mixture is heated at 110° C for 4 hours. After evaporation to dryness, 5% $K_2CO_3$ is added and the mixture is extracted with ethyl acetate. The extracts are washed with brine, dried over $Na_2SO_4$, filtered and evaporated to dryness. Addition of ethanol and petroleum ether to the residue affords solid product XI.

C.
5-endo-(1-naphthoyloxy)-N-(3-aminopropyl)bicyclo[2.2.1]heptane-endo-2,3-dicarboxylic acid imide hydrochloride (Ik)

A mixture of imide-nitrile XI (1.0 g; 2.96 mmole), 200 mg 10% Pd on carbon, 5 ml 5N HCl, and 95 ml ethanol is shaken under hydrogen at room temperature for 19 hours. After this time, water is added to the reaction mixture until all the solids dissolve. The catalyst is removed and the filtrate is evaporated to dryness, thereby affording the product Ik.

EXAMPLE 26

Preparation of
5-endo-(2-chloro-1-naphthoyloxy)-N-(3dimethylaminopropyl)bicyclo[2.2.1]heptane-2,3-di-endo-carboxylic acid imide [(±)-Iv].

Substitution in the procedure of example 6 for the 1-naphthoic acid chloride used therein of an equimolar quantity of 2-chloro-1-naphthoic acid chloride produces the title product (±)-Iv.

EXAMPLE 27

Preparation of
5-endo-(5-bromo-1-naphthoyloxy)-N-(3-dimethylaminopropyl)bicyclo[2.2.1]heptane-2,3-di-endo-carboxylic acid imide [(±)-Iw]

Substitution in the procedure of example 6 for the 1-naphthoic acid chloride used therein of an equimolar quantity of 5-bromo-1naphthoic acid chloride produces compound (±)-Ix.

EXAMPLE 28

Preparation of 5-endo-(2-hydroxy-1-naphthoyloxy)-N-(3-dimethylaminopropyl)bicyclo[2.2.1]heptane-2,3-di-endo-carboxylic acid imide [(±)-Ix]

Substitution in the procedure of example 6 for the 1-naphthoic acid chloride used therein of an equimolar quantity of 2-hydroxy-1naphthoic acid chloride produces the compound (±)-Ix.

EXAMPLE 29

Preparation of 5-endo-(8methyl-1-naphthoyloxy)-N-(3-dimethylaminopropyl)bicyclo[2.2.1]heptane2,3-di-endo-carboxylic acid imide [(±)-Iy]

Substitution in the procedure of example 6 for the 1-naphthoic acid used therein of an equimolar quantity of 8methyl-1-naphthoic acid chloride produces compound (±)-Iz.

EXAMPLE 30

Preparation of 5-endo-(2-ethyl-5-methoxy-1-naphthoyloxy-N-(3-dimethylaminopropyl)bicyclo-[2.2.1]heptane-2,3-di-endo-carboxylic acid imide [(±)-Iq]

Substitution in the procedure of example 6 for the 1-naphthoic acid chloride used therein of an equimolar quantity of 2-ethyl-5-methoxy-1-naphthoic acid chloride produces compound (±)-Iq.

EXAMPLE 31

Resolution of (±)-5-Endo-Naphthoyloxy-N-(3-dimethylaminopropyl)bicyclo[2.2.1]heptane-2,3-di-endo-carboxylic acid imide [(±)-Ib]

A.

(±)-5-endo-Naphthoyloxy-N-(3-dimethylaminopropyl)bicyclo[2.2.1]heptane-2,3-endo-carboxylic acid imide [(±)-Ib]

A stirred mixture of the hydrochloride salt of Ib (4.2 g) in water (100 ml) and EtOAc (200 ml) was neutralized by the addition of sodium carbonate. The layers were separated and aqueous layer was reextracted with EtOAc (2×100 ml). The combined EtOAc extracts were washed with water, and dried (sodium sulfate). The removal of the EtOAc left a colorless oil which was crystallized from hot cyclohexane to yield the racemic base Ib (3.6 g); m.p. 124°–5° C.

B. (+)-10-Camphorsulfonic acid salt of (−)-5-endo-naphthoyloxy-N-(3-dimethylaminopropyl)bicyclo[2.2.1]heptane-2,3-di-endo-carboxylic acid imide A hot solution of (+)-10-camphorsulfonic acid (1.16 g, 0.005 mole) in 90% ethanol (10ml) was added to a hot solution of the racemic base Ib (2.1 g, 0.005 mole) in 90% ethanol (30 ml). The solution was gently warmed and diluted with 90% ethanol (125 ml). The solution was filtered and cooled slowly to room temperature (23° C) at which time a colorless crystalline material formed. The crystalline material was collected and washed with 90% ethanol (50 ml) to yield the title product; (820 mg); m.p. 273°–274° C. The mother liquor was cooled to 0° C to yield a second crop of solid (658 mg); m.p. 270°–271° C. Both crops were combined and the salt was recrystallized from methanol-water (10:1) to give colorless needles (822 mg); m.p. 277°–278° C. The ethanolic mother liquor was saved for the isolation of the (+)-isomer.

C.

(−)-5-endo-Naphthoyloxy-N-(3-dimethylaminoproply)bicyclo[2.2.1]heptane-2,3-di-endo-carboxylic acid imide [(−)-Ib]

The camphorsulfonic acid salt from B above (500 mg) was partitioned between a stirred mixture of EtOAc (100 ml) and water (100 ml) containing sodium carbonate (5 g). The aqueous layer was reextracted with EtOAc (100 ml). The combined EtOAc extracts were dried (Na₂SO₄) and removal of the EtOAc left an oil which was crystallized from hot cyclohexane to yield a colorless solid (243 mg): m.p. 79°–80° C; $[\alpha]_D^{25}$ −74.67° (C = 0.920, ethanol).

D.

(−)-5-endo-Naphthoyloxy-N-(3-dimethylaminopropyl)bicyclo[2.2.1]heptane-2,3-di-endo-carboxylic acid imide hydrochloride [(−)-Ib HCl]

Hydrogen chloride gas was bubbled into a solution of the (−)-isomer (243 mg) in 100% ethanol (20 ml). The solution was cooled in ice. The colorless crystals were collected, washed well with EtOAc and dried to give title product; (114 mg); m.p. 183°–184° C; $[\alpha]_D^{25}$ −71.43° (C = 0.89, H₂O).

E.

(+)-5-endo-Naphthoyloxy-N-(3-dimethylaminopropyl)bicyclo[2.2.1]heptane-2,3-di-endo-carboxylic acid imide hydrochloride [(+)-Ib HCl]

The ethanolic mother liquor from the isolation of the levo isomer in B above was evaporated to dryness and the solid was partitioned between a stirred mixture of EtOAc (100 ml) and water (100 ml) containing sodium carbonate (5 g). The aqueous layer was reextracted with EtOAc (100 ml) and combined EtOAc extracts were washed with water and dried (Na₂SO₄). The removal of the EtOAc left an oil which was redissolved in 30 ml of ethanol. Hydrogen chloride gas was bubbled into the solution of the (+)-isomer. The solution was cooled in ice to yield a colorless solid identified as the title product (483 mg); m.p. 184°–185° C; $[\alpha]_D^{25}$ +71.60° (C = 0.74, H₂O).

We claim:
1. A compound having the formula

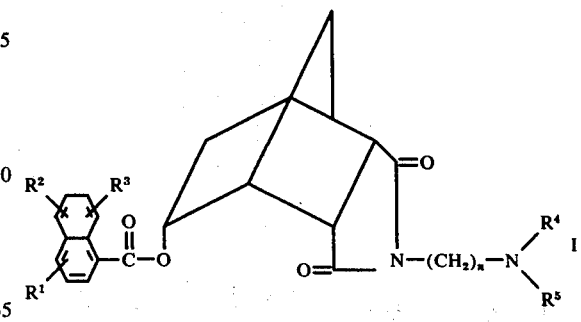

wherein R¹, R² and R³ are alike or different and each is H, Cl, Br, F, (lower)alkyl, nitro, OH or (lower)alkoxy, n is an integer of 2 to 4 inclusive and $R^4$ and $R^5$ are alike or different and each is H, (lower)alkyl or when taken together with the nitrogen a radical of the formula

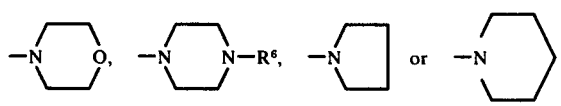

in which $R^6$ is (lower)alkyl; or a pharmaceutically acceptable acid addition salt thereof.

2. A compound of claim 1 having the formula

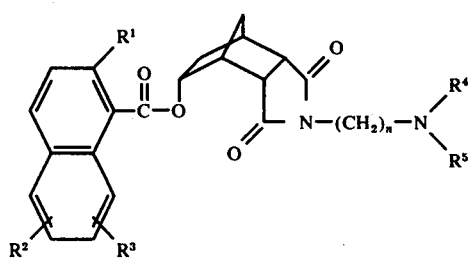

wherein $R^1$, $R^2$ and $R^3$ are alike or different and each is H, Cl, Br, F, (lower)alkyl, nitro, OH or (lower)alkoxy, n is an integer of 2 to 4 inclusive and $R^4$ and $R^5$ are alike or different and each is H, (lower)alkyl or when taken together with the nitrogen a radical of the formula

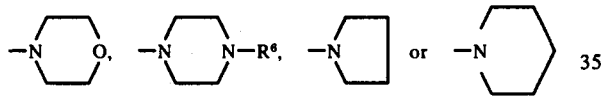

in which $R^6$ is (lower)alkyl; or a pharmaceutically acceptable acid addition salt thereof.

3. A compound of claim 1 having the formula

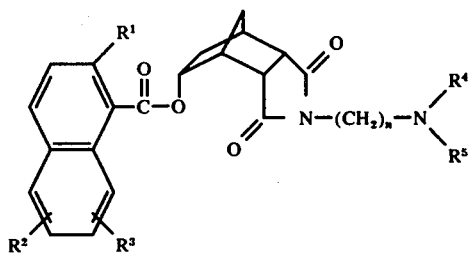

wherein $R^1$ is H or (lower)alkoxy, and $R^2$ and $R^3$ are alike or different and each is H, Cl, Br, F, (lower)alkyl, nitro, OH or (lower)alkoxy, n is an integer of 2 to 4 inclusive and $R^4$ and $R^5$ are alike or different and each is H, (lower)alkyl or when taken together with the nitrogen a radical of the formula

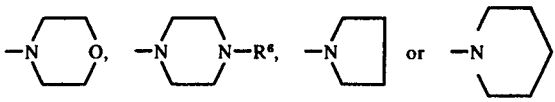

in which $R^6$ is (lower)alkyl; or a pharmaceutically acceptable acid addition salt thereof.

4. A compound of claim 1 having the formula

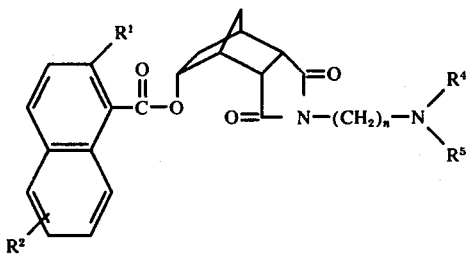

wherein $R^1$ and $R^2$ are alike or different and each is H, Cl, Br, F, (lower)alkyl, nitro, OH or (lower)alkoxy, n is an integer of 2 to 4 inclusive and $R^4$ and $R^5$ are alike or different and each is H, (lower)alkyl or when taken together with the nitrogen a radical of the formula

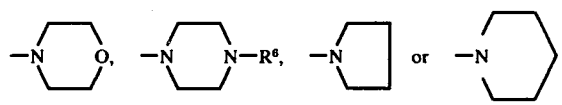

in which $R^6$ is (lower)alkyl; or a pharmaceutically acceptable acid addition salt thereof.

5. A compound having the formula

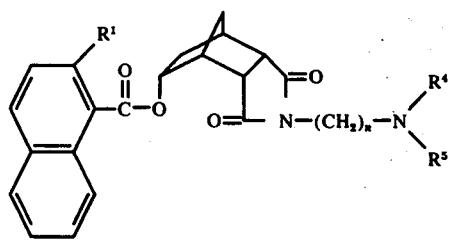

wherein $R^1$ is H, F, Cl, methoxy, ethoxy or n-propoxy, n is an integer of 2 to 4 inclusive and $R^4$ and $R^5$ are alike or different and each is H, (lower)alkyl or when taken together with the nitrogen a radical of the formula

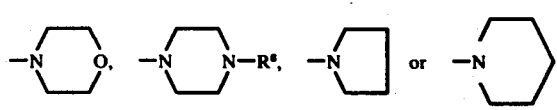

in which $R^6$ is (lower)alkyl; or a pharmaceutically acceptable acid addition salt thereof.

6. A compound of claim 1 having the formula

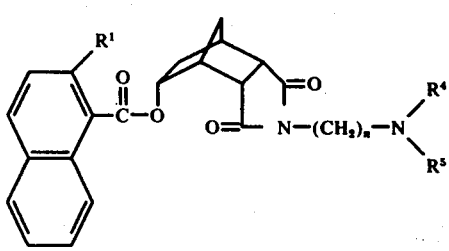

wherein $R^1$ is H, F, Cl, methoxy, ethoxy or n-propoxy, n is an integer of 2 to 4 inclusive and $R^4$ and $R^5$ are alike or different and each is H or (lower)alkyl; or a pharmaceutically acceptable acid addition salt thereof.

7. A compound of claim 6 having the formula

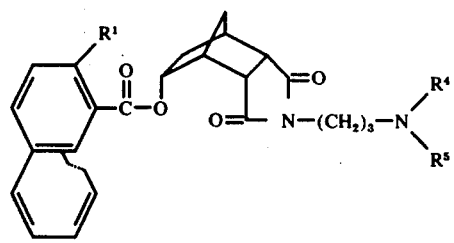

in which $R^1$ is H, methoxy or ethoxy, and $R^4$ and $R^5$ are alike or different and are H or (lower)alkyl; or a pharmaceutically acceptable acid addition salt thereof.

8. A compound having the formula

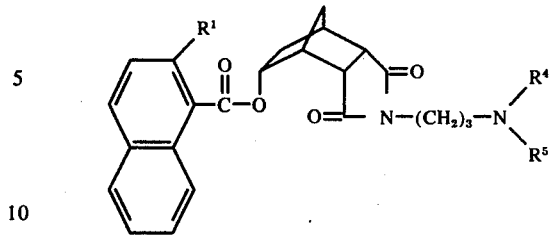

in which $R^1$ is methoxy or ethoxy, and $R^4$ and $R^5$ are alike or different and each is H, methyl or ethyl; or a pharmaceutically acceptable acid addition salt thereof.

9. A compound having the formula

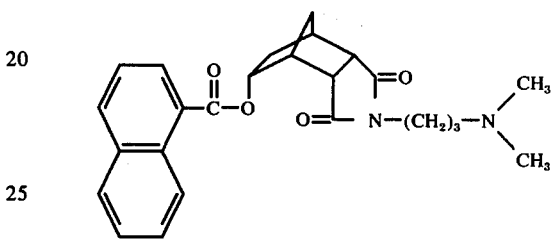

or the hydrochloride salt thereof.

10. The essentially pure levorotatory isomer of the compound of claim 9.

11. The essentially pure dextrorotatory isomer of the compound of claim 9.

12. The essentially pure dextrorotatory isomers of the compounds of claim 1.

13. The essentially pure levorotatory isomers of the compounds of claim 1.

14. The essentially pure levorotatory isomers of the compounds of claim 6.

15. The essentially pure dextrorotatory isomers of the compounds of claim 6.

* * * * *